United States Patent [19]

Knifton

[11] 4,390,734

[45] Jun. 28, 1983

[54] PROCESS FOR PRODUCING PROPYLENE GLYCOL MONOALKYL ETHERS FROM ACETALDEHYDE, AN ALKANOL AND SYNGAS USING A NEW CATALYST SYSTEM

[75] Inventor: John F. Knifton, Austin, Tex.

[73] Assignee: Texaco Inc., White Plains, N.Y.

[21] Appl. No.: 339,234

[22] Filed: Jan. 13, 1982

[51] Int. Cl.$^3$ .............................................. C07C 41/01
[52] U.S. Cl. .................... 568/678; 568/648; 568/670; 568/675; 568/387; 568/671
[58] Field of Search ................ 568/678, 670, 648, 675

[56] References Cited

U.S. PATENT DOCUMENTS

| | | | |
|---|---|---|---|
| 2,429,878 | 10/1947 | Gresham et al. | 568/678 |
| 4,071,568 | 1/1978 | Onada et al. | 568/678 |
| 4,144,401 | 3/1979 | Wall | 568/852 |
| 4,200,765 | 6/1980 | Goetz | 568/852 |

FOREIGN PATENT DOCUMENTS 875802  3/1953  Fed. Rep. of Germany ...... 568/678

*Primary Examiner*—Howard T. Mars
*Attorney, Agent, or Firm*—Carl G. Ries; Jack H. Park; Walter D. Hunter

[57] ABSTRACT

Propylene glycol monoalkyl ethers are prepared in good yield by reacting acetaldehyde and an alkanol (or by reacting an acetal) with carbon monoxide and hydrogen in the presence of a catalyst comprising a cobalt-containing compound and a cocatalyst comprising a member of the group consisting of rhodium-containing compounds, ruthenium-containing compounds and nickel-containing compounds, and heating the resulting mixture at moderate temperatures and pressures for sufficient time to produce the desired glycol monoalkyl ether, and then recovering the same from the reaction mixture.

21 Claims, No Drawings

PROCESS FOR PRODUCING PROPYLENE GLYCOL MONOALKYL ETHERS FROM ACETALDEHYDE, AN ALKANOL AND SYNGAS USING A NEW CATALYST SYSTEM

BACKGROUND OF THE INVENTION

1. Field of the Invention

This invention relates to a new process for preparing propylene glycol monoalkyl ethers. More particularly, the invention relates to an improved process for preparing propylene glycol monoalkyl ethers from acetaldehyde, an alkanol and syngas using a new catalyst system.

Specifically, the invention provides a new and improved process for preparing in good yield propylene glycol monoalkyl ethers from acetaldehyde and an alkanol (or reacting an acetal) with carbon monoxide and hydrogen in the presence of a catalyst comprising a cobalt-containing compound and a cocatalyst comprising a member of the group consisting of rhodium-containing compounds, ruthenium-containing compounds and nickel-containing compounds, and heating the resulting mixture at moderate temperatures and pressures for sufficient time to produce the desired glycol monoalkyl ether, and then recovering the same from the reaction mixture.

2. Prior Art

Glycol monoalkyl ethers have a wide variety of applications as solvents and reaction media. In the prior art, the glycol monoalkyl ethers are commercially produced by preparing an olefin oxide from an olefin and adding a suitable alcohol thereto. This method is based on the use of an olefin which is a petroleum product which is becoming costly to obtain. As a result, industry is seeking a new method for producing glycol monoalkyl ethers from starting materials other than olefins.

One proposed method is the reaction of an acetal with carbon monoxide and hydrogen in the presence of a cobalt carbonyl catalyst (West German Pat. Nos. 875,802 and 890,945). This method, however, suffers from the disadvantage of low selectivity of the glycol monoalkyl ether. U.S. Pat. No. 4,071,568 proposes the production of the glycol monoalkyl ethers by the same method using a catalyst made up of a cobalt compound and certain phosphorus or nitrogen-containing ligands. This method also suffers from the disadvantage of low yields of the desired glycol monoalkyl ether and the need to use relatively high pressures of the syngas.

It is an object of the invention, therefore, to provide a new process for preparing propylene glycol monoalkyl ethers. It is a further object to provide a new and improved method for preparing propylene glycol monoalkyl ethers from acetaldehyde, alcohols and syngas using a new catalyst system. It is a further object to provide a new process for preparing propylene glycol monoalkyl ethers from acetaldehyde, an alkanol and syngas which operates at moderate temperatures and moderate pressures. Other objects and advantages of the invention will be apparent from the following detailed description thereof.

SUMMARY OF THE INVENTION

It has now been discovered that these and other objects may be accomplished by the process of the invention which comprises contacting acetaldehyde and an alcohol, such as methanol, (or reacting an acetal) with carbon monoxide and hydrogen in the presence of a catalytic amount of a catalyst comprising a cobalt-containing compound, such as a cobalt carbonyl, and a cocatalyst comprising a member of the group consisting of a rhodium-containing compound, such as rhodium acetylacetonate, a ruthenium-containing compound, such as a ruthenium carbonyl, and a nickel-containing compound, such as nickel acetate, and heating the resulting mixture at moderate temperatures and pressures for sufficient time to produce the desired glycol monoalkyl ether, and then recovering the same from the reaction mixture. It was surprising to find that by the use of the above-noted cocatalysts one can obtain improved yields of the desired glycol ethers and can produce the same at much more moderate temperatures and pressures than utilized heretofore.

The process of the invention as far as the formation of the desired propylene glycol monoalkyl ethers is concerned may be represented by the following equation:

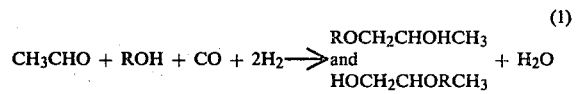

$$CH_3CHO + ROH + CO + 2H_2 \longrightarrow \begin{array}{l} ROCH_2CHOHCH_3 \\ \text{and} \\ HOCH_2CHORCH_3 \end{array} + H_2O \quad (1)$$

wherein the final product is a mixture of the alpha- and the beta-monoalkyl ethers.

The formation of the desired propylene glycol monoalkyl ether by the reaction of the syngas with the acetal may be represented by the following equation:

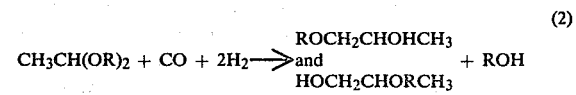

$$CH_3CH(OR)_2 + CO + 2H_2 \longrightarrow \begin{array}{l} ROCH_2CHOHCH_3 \\ \text{and} \\ HOCH_2CHORCH_3 \end{array} + ROH \quad (2)$$

Typical yields of the total propylene glycol monoalkyl ethers, based on acetal or acetaldehyde charged, range upwards from about 10 mole%. In general, the alpha-ether is obtained in greater amounts than the beta-ether. Other products obtained as minor by-products include the alkoxyacetones, dialkyl ethers, alcohols and the like.

DETAILED DESCRIPTION OF THE INVENTION

In the operation of the process of the invention, the propylene glycol monoalkyl ethers and above-noted by-products are prepared concurrently from acetaldehyde and an alkanol (or an acetal), carbon monoxide and hydrogen by a process comprising the following steps:

(a) contacting a mixture of the said acetaldehyde, alkanol, carbon monoxide and hydrogen with a catalytic amount of a catalyst comprising a cobalt-containing compound, such as cobalt carbonyl, and a cocatalyst selected from the group consisting of rhodium-containing compounds, ruthenium-containing compounds and nickel-containing compounds, (b) heating the said mixture at a moderate temperature of about 150° C. to 200° C., and a moderate operating pressure of about 1000 psi to about 5000 psi with sufficient carbon monoxide and hydrogen to satisfy the above-noted stoichiometry of the desired propylene glycol monoalkyl ether synthesis, until substantial formation of the glycol ether has been achieved, and, (c) preferably isolating the said propylene glycol monoalkyl ether, as by distillation.

In order to present the inventive concept of the present invention in the greatest possible detail, the following supplementary disclosure is submitted. The process of the invention is practiced as follows:

As noted, the catalyst system used in the process of the invention comprises a cobalt-containing compound and a cocatalyst selected from the group consisting of rhodium-containing compounds, ruthenium-containing compounds and nickel-containing compounds. The cobalt-containing compound may take many different forms. For instance, the cobalt may be added in the form of an oxide, salt, carbonyl derivative and the like. Examples of these include, among others, cobalt oxides, $Co_2O_3$, $Co_3O_4$, CoO, cobalt(II) bromide, cobalt(II) carbonate, cobalt(II) nitrate, cobalt(II) phosphate, cobalt acetate, cobalt naphthenate, cobalt benzoate, cobalt valerate, cobalt cyclohexanoate, cobalt carbonyls, such as dicobalt octacarbonyl $Co_2(CO)_8$, tetracobalt dodecacarbonyl $Co_4(CO)_{12}$ and hexacobalt hexadecacarbonyl $Co_6(CO)_{16}$ and derivatives thereof by reaction with ligands, and preferably group V donors, such as the phosphines, arsines, stibines, etc. derivatives, such as $(Co(CO)_3L)_2$ wherein L is $PR_3$, $AsR_3$ and $SbR_3$ wherein R is a hydrocarbon radical, cobalt carbonyl hydrides, cobalt carbonyl halides, cobalt nitrosyl carbonyls such as $CoNO(CO)_3$ and, $Co(NO)(CO)_2PPh_3$, cobalt nitrosyl halides, organometallic compounds obtained by reacting cobalt carbonyls with olefins, allyl and acetylene compounds, such as bis($\pi$-cyclopentadienyl)cobalt, ($\pi$-$C_5H_5$)$_2$Co, cyclopentadienylcobalt dicarbonyl, bis(hexamethylenebenzene)cobalt.

Preferred cobalt-containing compounds to be used in the catalyst system comprise those compounds having at least one cobalt atom attached to carbon, such as the cobalt carbonyls and their derivatives as, for example, dicobalt octacarbonyl, tetracobalt dodecacarbonyl, organometallic compounds obtained by reacting the cobalt carbonyls with olefin, cycloolefins, allyl and acetylene compounds such as cyclopentadienyl cobalt dicarbonyl, cobalt carbonyl halides, cobalt carbonyl hydrides, cobalt nitrosyl carbonyls, and the like, and mixtures thereof.

Particularly preferred cobalt-containing compounds to be used in the catalyst system comprise those having at least one cobalt atom attached to at least three separate carbon atoms, such as, for example, the dicobalt octacarbonyls and their derivatives.

The cocatalysts used with the above-noted cobalt-containing compounds comprise the members of the group consisting of rhodium-containing compounds, ruthenium-containing compounds and the nickel-containing compounds. The rhodium-containing compound may take many different forms. For instance, the rhodium may be added to the reaction mixture as an oxide, as in the case of, for example, rhodium(III) oxide hydrate, rhodium(IV) dioxide, and rhodium sesquioxide ($Rh_2O_3$). Alternatively, it may be added as the salt of a mineral acid, as in the case of rhodium(II) chloride hydrate, rhodium(III) bromide, rhodium(III) iodide, chlorodicarbonylrhodium(I) dimer, anhydrous rhodium(III) chloride and rhodium nitrate, or as the salt of a suitable organic carboxylic acid, for example, rhodium(II) formate, rhodium(II) acetate, rhodium(II) propionate, rhodium(II) butyrate, rhodium(II) valerate, rhodium(III) naphthenate, rhodium(III) acetylacetonate, etc. The rhodium may also be added as a carbonyl or hydrocarbonyl derivative. Here, suitable examples include tetrarhodium dodecacarbonyl, dirhodium octacarbonyl, hexarhodium hexadecacarbonyl, rhodium tetracarbonyl salts, and substituted carbonyl species such as rhodium dicarbonyl acetylacetonate.

Preferred rhodium-containing compounds include oxides of rhodium, rhodium salts of a mineral acid, rhodium salts of organic carboxylic acids and rhodium carbonyl or hydrocarbonyl derivatives. Among these, particularly preferred are rhodium(III) chloride, rhodium(III) acetylacetonate, rhodium sesquioxide, rhodium dicarbonyl acetylacetonate, rhodium(II) acetate, rhodium(II) propionate and hexarhodium hexadecacarbonyl.

The ruthenium-containing compound used as a cocatalyst may also be utilized in many different forms. It may be added as an oxide, as in the case of ruthenium-(IV) oxide hydrate, anhydrous ruthenium(IV) dioxide and ruthenium(VIII) tetraoxide. Alternatively, the cocatalyst may be added as the salt of a mineral acid, as in the case of ruthenium(III) chloride hydrate, ruthenium(III) bromide, ruthenium(III) iodide, tricarbonyl ruthenium nitrate, or as the salt of a suitable organic carboxylic acid, for example, ruthenium(III) acetate, ruthenium naphthenate, ruthenium valerate and ruthenium complexes with carbonyl-containing ligands such as ruthenium(III) acetylacetonate. The ruthenium may also be added to the reaction zone as a carbonyl or hydrocarbonyl derivative. Here, suitable examples include, among others, triruthenium dodecacarbonyl and other hydrocarbonyls such as $H_2Ru_4(CO)_{13}$ and $H_4Ru_4(CO)_{12}$, and substituted carbonyl speices such as the tricarbonylruthenium(II) chloride dimer, $(Ru(CO)_3Cl_2)_2$.

Preferred ruthenium-containing compounds include oxides of ruthenium, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl.

The nickel-containing cocatalyst may be chosen from a wide variety of organic or inorganic compounds, complexes, etc. as will be shown below. It is only necessary that the compound contain the nickel in any of its ionic states. For instance, the nickel may be added to the reaction mixture in an oxide form, as in the case of, for example, nickel(II) oxide (NiO), nickel(III) oxide ($Ni_2O_3.6H_2O$) and nickel (II,III) oxide (NiO, $Ni_2O_3$). Alternatively, it may be added as the salt of a mineral acid, as in the case of nickel(II) chloride ($NiCl_2$), nickel-(II) chloride hydrate ($NiCl_2.6H_2O$), nickel(II) bromide, nickel(II) bromide hydrate ($NiBr_2.H_2O$) nickel iodide ($NiI_2$), nickel(II) nitrate hydrate ($Ni(NO_3.6H_2O$) or as the salt of a suitable organic carboxylic acid, for example, nickel(II) naphthanate, nickel(II) formate, nickel-(II) acetate, nickel(II) propionate, nickel(III) acetylacetonate, etc. The nickel may also be added to the reaction zone as a carbonyl or hydrocarbonyl derivative. Here, suitable examples include nickel carbonyl ($Ni(CO_4)$), hydrocarbonyls and substituted carbonyl species such as bis(triphenylphosphine) nickel dicarbonyl, bis(triphenylphosphite) nickel dicarbonyl, etc.

Preferred nickel-containing compounds include oxides of nickel, nickel salts of mineral acids, nickel salts of organic carboxylic acids and nickel carbonyl or hydrocarbonyl derivatives. Among these, particularly preferred are nickel(II) acetylacetonate, nickel(II) acetate, nickel(II) propionate, and nickel carbonyl.

Typical combinations of catalyst and cocatalyst to be used in the process of the invention include, among others, dicobalt octacarbonyl-triruthenium dodeca carbonyl, dicobalt octacarbonyl-nickel acetate, dicobalt octacarbonyl-rhodium acetylacetone, cobalt bromide-rhodium trichloride/triethylphosphine, dicobalt octacarbonyl-ruthenium dichloride/triphenylphosphine complex, cobalt oxide-rhodium acetylacetonate, cobalt chloride-triruthenium dodecacarbonyl and the like.

The amount of the cobalt catalyst employed in the process of the invention is not critical and may vary over a wide range. In general, the process is desirable conducted in the presence of a catalytically effective quantity of one or more of the active cobalt species which gives the desired products in reasonable yields. The reaction proceeds when employing as little as about $1 \times 10^{-6}$ weight percent and lesser amounts of cobalt, based on the total weight of the reaction mixture. The upper concentration is dictated by a variety of factors including catalyst cost, partial pressures of carbon monoxide and hydrogen, operating temperature and choice of reactants. A cobalt catalyst concentration of from about $1 \times 10^{-5}$ to about 10 weight percent cobalt, based on the weight of reaction mixture, is generally desirable in the practice of this invention.

The cocatalysts may be employed in a wide range of concentrations. In general, the amount of the cocatalyst will vary from about 0.01 to about at least $10^2$ moles of cocatalyst per gram atom of cobalt present in the reaction mixture. Preferred ratios vary from about 0.1 to about 10.

The starting reactants in the process of the invention include acetaldehyde and an alkanol or an equivalent acetal. The alkanol selected will depend upon the alkyl group desired in the propylene glycol monoalkyl ether. Examples of suitable alkanols include, among others, methanol, ethanol, propanol, isopropanol, isobutanol, isoamyl alcohol, hexanol, and the like, and mixtures thereof. Preferred alkanols include the lower alkanols containing up to 10 carbon atoms, and still more preferably 1 to 4 carbon atoms.

Suitable acetals that can be used in the process of the invention in place of the acetaldehyde and alkanol include those obtained by reacting acetaldehyde with 2 moles of the above-noted alkanols, such as, for example, acetal, diethyl acetal, dipropyl acetal, diamyl acetal, diisopropyl acetal and dihexyl acetal.

The amount of the acetaldehyde and alkanol (or acetal) to be used in the process of the invention may vary over a wide range. In general, the amount of the acetaldehyde and alkanol to be used should be sufficient to satisfy the stoichiometry of the formation of the propylene glycol monoalkyl ethers as shown in equation 1 above, although larger or smaller amounts may be used as desired or necessary. Preferably the alkanol to acetaldehyde molar ratios are employed in amounts varying from about 2 to about 10.

The relative amounts of carbon monoxide and hydrogen which may be initially present in the syngas mixture can be varied widely. In general, the mole ratio of CO to $H_2$ is in the range from about 20:1 to 1:20, preferably from about 5:1 to 1:5. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon and the like, or they may include gases that may or may not undergo reaction under CO hydrogenation conditions, such as methane, ethane, propane, and the like, ethers such as dimethyl ether and diethyl ether.

The temperature used in the process of the invention may vary over a considerable range, but as noted above, a distinct advantage of the present process is that it can operate at the more moderate temperatures such as, for example, those within the range of 100° C. to about 250° C. The exact temperature selected will depend upon experimental factors, such as the pressure, the concentration and choice of the particular catalyst and cocatalyst selected, etc. Preferred temperatures range from about 150° C. to about 250° C.

Superatmospheric pressures of say at least 500 psi or greater lead to substantial yields of the desired glycol ethers. A distinct advantage of the present process over many of the known techniques involves the use of the more moderate pressures, e.g. pressures below about 5000 psi. In general, autogenous pressures varying from about 1000 psi to about 5000 psi give good results and are generally preferred. The pressures referred to herein represent the total pressure generated by all the reactants at the reaction temperature, although they are substantially due to the carbon monoxide and hydrogen reactants.

The desired products of the reaction will be the propylene glycol monoalkyl ethers. Examples of these include among others, propylene glycol monomethyl ether, propylene glycol monobutyl ether, propylene glycol monopropyl ether, propylene glycol monohexyl ether, propylene glycol monoheptyl ether, propylene glycol monoallyl ether, propylene glycol monophenyl ether, propylene glycol monocyclohexyl ether, propylene glycol monocyclopentyl ether and propylene glycol monodecyl ether. As noted above, these products will generally consist of a mixture of the alpha-ether and the beta-ether with the alpha-ether being formed in larger amounts.

Other products of the reaction include minor by-products such as the alkoxyacetones, dialkyl ethers, alkanols and the like. The desired products and by-products can be recovered from the reaction mixture by conventional means, such as fractional distillation in vacuo, etc.

The process of the invention can be conducted in batch, semi-continuous or continuous manner. The catalyst and cocatalyst can be initially introduced into the reaction zone batchwise, or they may be continuously or intermittently introduced into such a zone during the course of the synthesis reaction. Operation conditions can be adjusted to optimize the formation of the desired ethers, and said material can be recovered by methods known to the art, such as distillation, fractionation, extraction and the like. A fraction rich in the catalyst and cocatalyst may then be recycled to the reaction zone, if desired, and additional product generated.

The products have been identified in this work by one or more of the following analytical procedures; viz, gas-liquid phase chromatography (glc), infrared (ir) mass spectrometry, nuclear magnetic resonance (nmr) and elemental analyses, or a combination of these techniques. Analyses have, for the most part, been by parts by weight; all temperatures are in degrees centigrade and all pressures in pounds per square inch (psi).

To illustrate the process of the invention, the following examples are given. It is to be understood, however, that the examples are given in the way of illustration and are not to be regarded as limiting the invention in any way.

EXAMPLE I

This example illustrates the improved results obtained by using the new catalyst system in the formation of the propylene glycol monoalkyl ethers.

To a 450 ml glass-lined pressure reactor is charged a mixture of dicobalt octacarbonyl (2.0 mmole CO), rhodium(III) acetylacetonate (1.0 mmole). To this mixture is added 0.3 moles of ethanol and 0.1 mole of acetal. The mixture is charged under a nitrogen atmosphere, the reactor sealed, flushed with $CO/H_2$ (1:2), pressured to 2700 psi with 1:2 $CO/H_2$ and then heated to 160° C. with agitation for 4 hours. The autogenous pressure in the reactor reached a maximum of 3800 psi.

After carbonylation, the reactor is cooled and the gas pressure noted (2350 psi), the excess gas sampled and vented, and the deep red solution product (29.1 g) recovered.

Analysis of the liquid product by glc and Karl Fischer titration shows it to contain:
- 7.2% propylene glycol alpha-monoethyl ether
- 2.1% propylene glycol beta-monoethyl ether
- 0.8% ethoxyacetone
- 2.9% water
- 4.0% diethyl ether
- 74.2% ethanol
- 0.2% acetaldehyde Estimated yield of propylene glycol monethyl ethers (basis acetal charged) is 28 mole%.

Typical off gas samples show the presence of:
- 62% hydrogen
- 35% carbon monoxide
- 20% carbon dioxide Cobalt recovery in solution is greater than 98% of that originally charged. There is no solid product phase.

The propylene glycol monoethyl ethers are recovered from the crude liquid product by fractional distillation in vacuo.

EXAMPLE I

Comparative Tests

The following experiments demonstrate the surprising nature of the above-noted results in relation to results obtained with other catalyst systems.

Comparative Example A

The reactor is charged with a mixture of rhodium-(III) acetylacetonate (1.0 mmole) triethylphosphine (3.5 mmole) and acetal (0.1 mole) in 13.8 grams of ethanol (0.3 mole). There is no cobalt-containing material in this run. The mixture is pressured to 2700 psi with 1:2 $(CO/H_2)$ syngas, then the reactor is heated to 160° C. for 4 hours with agitation. The autogenous pressure in the reactor reached a maximum of 3800 psi.

On cooling the gas pressure (2340 psi) is noted, the excess gas sampled and vented and the deep-red liquid product (26.7 g) recovered.

Analysis of the liquid product by glc and Karl Fischer titration shows it to contain:
- 0.7% propylene glycol alpha-monoethyl ether
- 0.6% propylene glycol beta-monoethyl ether
- 0.6% water
- 3.5% diethyl ether
- 84.8% ethanol Estimated yield of propylene glycol monoethyl ethers (basis acetal charged) is 3.3 mol%.

Yield of ethoxyacetone (based on acetal charged) is 1 mol%.

Typical off-gas sample show the presence of:
- 59% hydrogen
- 39% carbon monoxide
- 1.1% carbon dioxide.

Comparative Example B

In another experiment, the reactor is charged with a mixture of cobalt octacarbonyl (2.0 mmole CO) and acetal (0.1 mole) in 13.8 g of ethanol (0.3 mole). There is no rhodium-containing component or phosphine in this run. The mixture is pressured to 2700 psi with 2:1 $(H_2/CO)$ syngas, then the reactor is heated to 160° C. for 4 hours with agitation.

On cooling, the gas pressure (2300 psi) is noted, the excess gas sampled and vented and the deep-red liquid product (28.9 g) recovered.

Analysis of the liquid product by glc and Karl Fischer titration shows it to contain:
- 2.1% propylene glycol alpha-monoethyl ether
- 2.2% propylene glycol beta-monoethyl ether
- 8.7% ethoxyacetone
- 2.2% water
- 1.7% diethyl ether
- 0.3% acetal
- 71.8% ethanol Estimated yield of propylene glycol monoethyl ethers (basis acetal charged) is 12 mol%.

Yield of ethoxyacetone (basis acetal charged) is 25 mol%.

Typical off-gas sample show the presence of:
- 62% hydrogen
- 27% carbon monoxide
- 49% carbon dioxide

EXAMPLE II

The procedure of Example I was repeated with the exception that the reactor is charged with a mixture of dicobalt octacarbonyl (2.0 mmole Co), rhodium(III) chloride (1.0 mmole), triethylphosphine (3.5 mmole) and acetal (0.1 mole) in 13.8 grams of ethanol (0.3 mole). The mixture is charged under a nitrogen atmosphere, the reactor is sealed, flushed with $CO/H_2$ (1:2), pressured to 2700 psi with 1:2 syngas $(CO/H_2)$ and then heated to 160° C. with agitation for 4 hours. The autogenous pressure in the reactor reaches a maximum of 3900 psi.

On cooling the gas pressure is noted (2300 psi), the excess gas sampled and vented and the red liquid product (28.4 g) recovered. Analysis of the liquid product by glc and Karl Fischer titration shows it to contain the following:
- 5.1% propylene glycol alpha-monoethyl ether
- 1.3% propylene glycol beta-monoethyl ether
- 0.2% ethoxyacetone
- 1.7% water
- 5.6% diethyl ether
- 78.4% ethanol
- 0.1% acetaldehyde Estimated yield of propylene glycol monoethyl ethers (basis acetal charged) is 18 mol%.

Typical off-gas samples show the presence of:
- 64% hydrogen
- 32% carbon monoxide
- 1.9% carbon dioxide Cobalt recovery in solution is 96% of that originally charged. There is no solid product fraction.

The propylene glycol monoethyl ethers are recovered from the crude liquid product by fractional distillation in vacuo.

EXAMPLE III

The procedure of Example I was repeated with the exception that the catalyst consisted of 1.0 mmole dicobalt octacarbonyl and 0.16 mmole of triruthenium dodecylcarbonyl. The temperature was maintained at 160° C. with an initial pressure of 2700 psi and a maximum autogenous pressure of 3825 psi for a reaction period of 4 hours. Analysis of the resulting liquid product showed the following:

3.6% propylene glycol alpha-ethyl ether
3.3% propylene glycol beta-ethyl ether
4.3% ethoxyacetone
0.1% acetal
3.9% water
70.4% ethanol Estimated yield of propylene glycol monoethyl ethers (basis acetal charged) is 20 mole%.

Cobalt recovery in solution is 98% of that originally charged. There is no solid product fraction.

EXAMPLE IV

The procedure of Example I was repeated with the exception that the catalyst composition comprised 1.0 mmole dicobalt octacarbonyl and 0.5 mmole of $(PPh_3)_2(CO)_2RuCl_2$. The temperature was maintained at 160° C. with an initial pressure of 2700 psi and a maximum autogenous pressure of 3800 psi for a reaction period of 4 hours.

Analysis of the resulting liquid product showed the following:

5.1% propylene glycol alpha-ethyl ether
2.0% propylene glycol beta-ethyl ether
3.7% ethoxyacetone
1.8% acetal
2.6% water
75.8% ethanol
2.5% diethyl ether
Cobalt recovery was 98%

EXAMPLE V

The procedure of Example I was repeated with the exception that the catalyst composition comprised 1.0 mmole of dicobalt octacarbonyl and 0.5 mmole of $(PPh_3)_3RuCl_2$. The temperature was maintained at 160° C. with an initial pressure of 2700 psi and a maximum autogenous pressure of 3800 psi for a reaction period of 4 hours.

Analysis of the resulting liquid product showed the following:

5.1% propylene glycol alpha-ethyl ether
2.1% propylene glycol beta-ethyl ether
4.1% ethoxyacetone
1.3% acetal
2.6% water
75.5% ethanol
2.4% diethyl ether
Cobalt recovery was 87%

EXAMPLE VI

The procedure of Example I was repeated with the exception that the catalyst consisted of 2.0 mmole of dicobalt octacarbonyl, 1.0 mmole of nickel acetate. The temperature was maintained at 160° C., the initial pressure is 2700 psi and for 4 hour reaction period the maximum autogenous pressure is 3775 psi. Analysis of the liquid product showed the following:

3.3% propylene glycol alpha-ethyl ether
2.3% propylene glycol beta-ethyl ether
5.2% ethoxyacetone
0.2% acetal
2.8% water
69.6% ethanol

EXAMPLE VII

The procedure of Example I was repeated with the exception that the catalyst consisted of 1.0 mmole of dicobalt octacarbonyl, 0.5 mmole of rhodium triacetylacetonate. The temperature was maintained at 160° C., the initial pressure is 2700 psi and for a 4 hour reaction period the maximum autogenous pressure is 3875 psi.

Analysis of the resulting liquid product showed the following:

5.2% propylene glycol alpha-ethyl ether
1.7% propylene glycol beta-ethyl ether
1.9% ethoxyacetone
3.9% water
69.9% ethanol

EXAMPLE VIII

The procedure of Example I was repeated with the exception that the catalyst consisted of 0.5 mmole of dicobalt octacarbonyl, 1.0 mole of rhodium(III) acetylacetonate and 3.5 mmole triethylphosphine. The temperature was maintained at 160° C., the initial pressure is 2700 psi and for a 4 hour reaction period the maximum autogenous pressure is 4050 psi. Analysis of the resulting liquid product showed the following:

3.4% propylene glycol alpha-ethyl ether
2.5% propylene glycol beta-ethyl ether
1.5% ethoxyacetone
1.2% water
78.9% ethanol
4.0% diethyl ether
Cobalt recovery was greater than 98%.

What is claimed is:

1. A process for producing propylene glycol monoalkyl ethers from acetaldehyde and an alkanol or acetal which comprises contacting a mixture of acetaldehyde and alkanol, or an equivalent acetal, with carbon monoxide and hydrogen in the presence of a catalytic amount of a catalyst consisting of a cobalt-containing compound and a cocatalyst selected from the group consisting of rhodium-containing compounds, ruthenium-containing compounds, and nickel-containing compounds, and heating the mixture at moderate temperatures and moderaate pressures for sufficient time to produce the desired glycol monoalkyl ether, and then recovering the same from the reaction mixture.

2. A process as in claim 1 wherein the alkanol contains from 1 to 10 carbon atoms.

3. A process as in claim 1 wherein the alkanol is methanol.

4. A process as in claim 1 wherein the cobalt-containing compound is a member of the group consisting of cobalt carbonyls and derivatives thereof obtained by reacting the carbonyls with a group V donor ligand, cobalt carbonyl hydrides, cobalt carbonyl halides, cobalt nitrosyl carbonyls, cycloalkadienyl cobalt carbonyls, cobalt halides, cobalt oxides and cobalt salts of organic carboxylic acids.

5. A process as in claim 1 wherein the cobalt-containing compound is a cobalt compound having at least one cobalt from linked to at least three separate carbon atoms.

6. A process as in claim 1 wherein the rhodium cocatalyst is a member of the group consisting of rhodium(III) chloride, rhodium sesquioxide, rhodium(III) acetylacetonate, rhodium dicarbonyl acetylacetonate, rhodium(III) acetate, rhodium(II) propionate and hexarhodium hexadecacarbonyl.

7. A process as in claim 1 wherein the ruthenium-containing compound is a member of the group consisting of one or more oxides of ruthenium, ruthenium complexes or carbonyl-containing ligands, ruthenium salts of organic acids and ruthenium-carbonyl and hydrocarbonyl compounds.

8. A process as in claim 1 wherein the ruthenium-containing compound is a member of the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate, and triruthenium dodecacarbonyl.

9. A process as in claim 1 wherein the nickel-containing compound is a member of the group consisting of one or more oxides of nickel, nickel salts of a mineral acid, nickel salts of an organic carboxylic acid and nickel carbonyl or hydrocarbonyl derivatives.

10. A process as in claim 1 wherein the nickel-containing compound is selected from the group consisting of nickel(II) chloride, nickel(II) oxide, nickel(II) acetylacetonate, nickel(II) acetate, nickel(II) propionate and nickel carbonyl.

11. A process as in claim 1 wherein the cobalt-containing catalyst is a cobalt carbonyl.

12. A process as in claim 1 wherein the rhodium cocatalyst is a rhodium acetylacetonate.

13. A process as in claim 1 wherein the ruthenium-containing cocatalyst is a ruthenium carbonyl.

14. A process as in claim 1 wherein the nickel-containing cocatalyst is a nickel salt of a lower alkanoic acid.

15. A process as in claim 1 wherein the carbon monoxide and hydrogen are employed in a mole ratio varying from 4:1 to 1:4.

16. A process as in claim 1 wherein the catalyst components are combined in a mole ratio of cobalt-containing compound to cocatalyst of 1:0.1 to 1:10.

17. A process as in claim 1 wherein the reaction is conducted at a temperature between about 100° C. and 250° C.

18. A process as in claim 1 wherein the reaction is conducted at a pressure varying from about 500 psi to about 5000 psi.

19. A process as in claim 1 wherein the cobalt-containing compound is a dicobalt octacarbonyl.

20. A process as in claim 1 wherein the reactant is acetal.

21. A process for producing propylene glycol monoalkyl ethers from acetal which comprises reacting the acetal with carbon monoxide and hydrogen in the presence of a catalytic amount of a catalyst consisting of a cobalt carbonyl and a cocatalyst selected from the group consisting of rhodium-containing compounds, ruthenium-containing compounds and nickel-containing compounds, and heating the mixture to a temperature between 100° C. and 250° C. at a pressure of 500 psi to 5000 psi for sufficient time to produce the desired glycol ether.

* * * * *

UNITED STATES PATENT AND TRADEMARK OFFICE
CERTIFICATE OF CORRECTION

PATENT NO. : 4,390,734
DATED : June 28, 1983
INVENTOR(S) : John Frederick Knifton It is certified that error appears in the above-identified patent and that said Letters Patent are hereby corrected as shown below:

Claim 5, column 11, line 1, "from" should read --atom--.

Signed and Sealed this

Thirteenth Day of September 1983

[SEAL]

Attest:

GERALD J. MOSSINGHOFF

Attesting Officer

Commissioner of Patents and Trademarks